(12) United States Patent
O'Brien et al.

(10) Patent No.: US 6,602,674 B1
(45) Date of Patent: Aug. 5, 2003

(54) USES OF ANTILEUKOPROTEASE IN CARCINOMA

(75) Inventors: Timothy J. O'Brien, Little Rock, AR (US); Lowell J. Underwood, Little Rock, AR (US); Hirotoshi Tanimoto, Kagawa (JP); Kazushi Shigemasa, Hiroshima (JP)

(73) Assignee: The Board of Trustees of the University of Arkansas, Little Rock, AR (US)

( * ) Notice: Subject to any disclaimer, the term of this patent is extended or adjusted under 35 U.S.C. 154(b) by 174 days.

(21) Appl. No.: 09/692,820

(22) Filed: Oct. 18, 2000

Related U.S. Application Data (60) Provisional application No. 60/159,972, filed on Oct. 18, 1999.

(51) Int. Cl.$^7$ .................. G01N 33/574; G01N 33/49
(52) U.S. Cl. .................. 435/7.23; 436/501; 436/64
(58) Field of Search .................. 435/7.1, 23, 6, 435/7.4, 7.23; 530/350; 436/501, 64

(56) References Cited

PUBLICATIONS

Koshikawa et al (1996, Journal of Biochemistry 119: 334–339).*
MacDonald et al (1998, Annals Academy of Medicine Singapore 27: 676–82, Abstract only).*

* cited by examiner

*Primary Examiner*—Sheela Huff
*Assistant Examiner*—Misook Yu
(74) *Attorney, Agent, or Firm*—Benjamin Aaron Adler (57) ABSTRACT

The present invention provides a method of detecting/monitoring tumor growth and progression in a tissue by measuring the level of antileukoprotease. Also provided is a method of treating an individual having a tumor by administering antileukoprotease to inhibit the activity of stratum corneum chymotryptic enzyme. Specifically, the tumor is an ovarian carcinoma.

5 Claims, 6 Drawing Sheets

SEQUENCE LISTING

<160> NUMBER OF SEQ ID NOS: 6

<210> SEQ ID NO 1
<211> LENGTH: 17
<212> TYPE: DNA
<213> ORGANISM: Artificial sequence
<220> FEATURE:
<223> OTHER INFORMATION: Forward oligonucleotide primer for
      amplification of antileukoprotease

<400> SEQUENCE: 1
tgcattgaca acgaggc                                                      17

<210> SEQ ID NO 2
<211> LENGTH: 17
<212> TYPE: DNA
<213> ORGANISM: Artificial sequence
<220> FEATURE:
<223> OTHER INFORMATION: Reverse oligonucleotide primer for PCR
      amplification of antileukoprotease

<400> SEQUENCE: 2

```
ctgtcttgac attgttg                                                    17

<210> SEQ ID NO 3
<211> LENGTH: 20
<212> TYPE: DNA
<213> ORGANISM: Artificial sequence
<220> FEATURE:
<223> OTHER INFORMATION: Forward oligonucleotide primer for PCR
      amplification of antileukoprotease

<400> SEQUENCE: 3
ccttcaaagc tggagtctgt                                                 20

<210> SEQ ID NO 4
<211> LENGTH: 20
<212> TYPE: DNA
<213> ORGANISM: Artificial sequence
<220> FEATURE:
<223> OTHER INFORMATION: Reverse oligonucleotide primer for PCR
      amplification of antileukoprotease

<400> SEQUENCE: 4
ccaaaggagg atatcagtgg                                                 20

<210> SEQ ID NO 5
<211> LENGTH: 20
<212> TYPE: DNA
<213> ORGANISM: Artificial sequence
<220> FEATURE:
<223> OTHER INFORMATION: Forward oligonucleotide primer for PCR
      amplification of β-tubulin

<400> SEQUENCE: 5
cgcatcaacg tgtactacaa                                                 20

<210> SEQ ID NO 6
<211> LENGTH: 20
<212> TYPE: DNA
<213> ORGANISM: Artificial sequence
<220> FEATURE:
<223> OTHER INFORMATION: Forward oligonucleotide primer for PCR
      amplification of β-tubulin

<400> SEQUENCE: 6
tacgagctgg tggactgaga                                                 20
```

USES OF ANTILEUKOPROTEASE IN CARCINOMA

CROSS-REFERENCE TO RELATED APPLICATION

This non-provisional patent application claims benefit of provisional patent application U.S. Ser. No. 60/159,972, filed Oct. 18, 1999, now abandoned.

BACKGROUND OF THE INVENTION

1. Field of the Invention

The present invention relates generally to the fields of protein chemistry and cancer therapy. More specifically, the present invention relates to antileukoprotease, a peptide inhibitor of stratum corneum chymotryptic enzyme, and its uses in carcinoma diagnosis and treatment.

2. Description of the Related Art

Proteases mediate specific proteolysis involved in processing of precursors of protein hormones, activation of regulatory enzymes in blood coagulation and complement activation, and the tissue rearrangement involved in tumor progression (1). In the process of tumor invasion and metastasis, proteases mediate the digestion of neighboring extracellular matrix components during initial tumor growth. This allows shedding of minor cells into the surrounding environment, providing the basis for invasion of basement membranes in target metastatic organs. Proteolytic digestion is also required for release and activation of many growth and angiogenic factors (2–4).

A large number of reports have demonstrated increased production of several classes of proteases, including matrix metalloproteases (MMP's), cysteine proteases, aspartic proteases and serine proteases in tumor cells (5–9). The proteolysis of the extracellular matrix is a highly complicated process, which probably involves a cascade of events requiring a variety of proteases (10). In this cascade, the integrated capacity for extracellular matrix digestion, tumor cell invasion, and metastatic growth may be mediated by proteases with unique specificities. This hypothesis is supported by findings that some agents specifically inhibit one of these proteases to reduce tumor cell invasion (11,12).

Stratum corneum chymotryptic enzyme (SCCE) was originally isolated from a keratinocyte derived library and was identified as a serine protease (13,14). Analysis of mRNA showed that two transcripts of 1.2 kb and 2.0 kb were present, and abundant expression of the stratum corneum chymotryptic enzyme gene was restricted to human skin. Immunohistochemical studies confirmed that stratum corneum chymotryptic enzyme was a tissue-specific enzyme only expressed by the stratum corneum (15). The nucleotide sequence includes an open reading frame for a stratum corneum chymotryptic enzyme precursor protein consisting of 253 amino acids. This inactive precursor becomes proteolytically active after tryptic removal of a 7 amino acid peptide from the amino terminal end of the propeptide. Recent studies have revealed that stratum corneum chymotryptic enzyme appears to catalyze the degradation of intercellular cohesive structures between corneocytes in the outermost cornified layer of the skin and contributes to the cell shedding process at the skin surface (14, 16, 17). This process occurs possibly through the degradation of matrix components including the desmosomal protein desmoglein I.

Protease inhibitor antileukoprotease (ALP), also known as secretory leukocyte proteinase inhibitor (SLPI), has been identified as a potent inhibitor of leukocyte elastase, cathepsin G, chymotrypsin and trypsin (18). Antileukoprotease has been cloned from skin tissue and shown to be a specific inhibitor of the stratum corneum chymotryptic enzyme (SCCE) (17). This serine protease is produced and released into mucus by secretory cells in the parotid, bronchus, cervix and testicular glands (18). There, it is thought to play a physiological role in preventing the proteolytic degradation of these tissues. However, little has been known about the expression of antileukoprotease in human cancer tissues, including ovarian cancer.

The prior art is deficient in the lack of effective means of using antileukoprotease as a diagnostic or monitoring tool of carcinomas. The present invention fulfills this long-standing need and desire in the art.

SUMMARY OF THE INVENTION

The present invention demonstrates that antileukoprotease (ALP) is overexpressed in low malignant potential tumors and carcinomas in ovary, while little or no transcript is present in normal adult and fetal tissues. This indicates that antileukoprotease may be used as a diagnostic or monitoring tool of ovarian tumors.

In one embodiment of the present invention, there is provided a method of detecting an ovarian or ovarian-derived metastatic tumor in an individual suspected to have such a tumor, comprising the step of detecting the level of antileukoprotease in a test tissue, a secretion from a test tissue or the blood. If the level exceeds the mean basal level of antileukoprotease in nondiseased individuals by 2 standard deviations or more, the individual has an ovarian or ovarian-derived metastatic tumor.

In still another embodiment of the present invention, there is provided a method of treating an individual having a ovarian tumor by administering antileukoprotease to the individual.

In yet another embodiment of the instant invention, a method of preventing metastasis of an ovarian tumor is provided wherein antileukoprotease is administered to an individual having such a tumor.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1A confirms the presence of antileukoprotease transcript in tumor tissues as opposed to normal tissues. ALP mRNA was detected as a 1.4 kb transcript in ovarian cancers but was not detected in normal ovary. FIG. 1B shows that the antileukoprotease transcript was not detected in fetal tissues. FIG. 1C and FIG. 1D show that antileukoprotease transcript was not detected in many normal adult tissues but was abundantly expressed in others including lung.

FIG. 4A shows immunohistochemical staining or normal uterine endocervix at 5×magnification. The endocervix section acts as a positive control as normal endocervical glandular cells and the mucin in the endocervical glands is positive for ALP. FIG. 4B, showing a 100×magnification of normal ovarian surface epithelium, is negative for antileukoprotease immunohistochemical staining. Positive antileukoprotease immunohistochemical staining was observed in both the cell membrane and cytoplasm of ovarian cancer cells of FIG. 4C (endometrioid adenocarcinoma, ×50). In FIG. 4D (mucinous adenocarcinoma, ×50), the mucin as well as tumor glands of a mucinous carcinoma were positive for antileukoprotease staining. Positive staining for antileukoprotease was also observed in secretions from the clear cell carcinoma shown in FIG. 4E (clear cell carcinoma, ×50) and in the serous carcinomas shown in FIGS. 4F and 4G.

DETAILED DESCRIPTION OF THE INVENTION

This invention encompasses a demonstration of overexpression of antileukoprotease (ALP) in carcinoma tissues. It shows that many low malignant potential tumors and most carcinomas tested have a statistically significant overexpression of antileukoprotease. Antileukoprotease is a secreted protein with a distribution of cysteines known to provide extraordinary stability to protease inhibitors. This molecule therefore fulfills many criteria necessary for a valuable marker of tumor growth and progression. Antileukoprotease is overexpressed in tumor cells secreted to the extracellular space and is a relatively small protein (approximately 100 amino acids) providing good opportunity for uptake into the circulation. Moreover, antileukoprotease is a very stable protein thus providing the potential for a relatively long half life in the circulation.

In one embodiment of the present invention, there is provided a method of detecting growth of an ovarian or ovarian-derived metatatic tumor in an individual suspected of having such a tumor, comprising the step of detecting the level of antileukoprotease in a test sample, wherein if the level exceeds the mean basal level of antileukoprotease in nondiseased individuals by 2 standard deviations or greater, the individual has an ovarian or ovarian-derived tumor.

Preferably, the tumor may be a low malignant potential tumor or a carcinoma. Examples of carcinoma include serous carcinoma, mucinous carcinoma, endometrioid carcinoma and clear cell carcinoma. The test samples may be an ovarian secretion, an ovarian biopsy, a metastatic tumor biopsy and blood. The antileukoprotease may be detected by various means know to one having ordinary skill in this art including western blot analysis, immunohistochemical staining, or other immunochemical methods. In still another embodiment of the present invention, there is provided a method for treating an individual having an ovarian or ovarian-derived metastatic tumor, comprising the step of administering antileukoprotease to the individual. Preferably, the tumor may be a low malignant potential tumor or an ovarian carcinoma. If it is an ovarian carcinoma, the tumor may be a serous carcinoma, a mucinous carcinoma, an endometrioid carcinoma and a clear cell carcinomas. The antileukoprotease may be administered systemically or locally.

In yet another embodiment of the present invention, there is provided a method for method of preventing metastasis of an ovarian tumor or ovarian derived metastatic tumor comprising the step of administering antileukoprotease to an individual having such a tumor. Preferably, the tumor may be a low malignant potential tumor or an ovarian carcinoma. If it is an ovarian carcinoma, the tumor may be a serous carcinoma, a mucinous carcinoma, an endometrioid carcinoma and a clear cell carcinomas. The antileukoprotease may be administered systemically or locally.

The following examples are given for the purpose of illustrating various embodiments of the invention and are not meant to limit the present invention in any fashion.

EXAMPLE 1

Tissue Samples

Fresh surgical specimens of ovarian tumors were obtained from low malignant potential tumors and carcinomas. Clinical staging was determined according to the criteria of the International Federation of Gynecology and Obstetrics (FIGO). Normal ovaries were obtained from patients who underwent surgery for benign gynecological disease. The materials were obtained immediately after the surgical procedures and frozen in liquid nitrogen and stored at −80° C. prior to mRNA isolation. Two ovarian cancer cell lines, SW626 and CaOv3, were also used.

EXAMPLE 2 mRNA Extraction and cDNA Synthesis

Extraction of mRNA from tissue specimens and cDNA synthesis therefrom were carried out by the methods described previously (19). mRNA was isolated by using a RiboSep™ mRNA isolation kit (Becton Dickenson Labware). In this procedure, poly A+ mRNA was isolated directly from the tissue lysate using the affinity chromatography media oligo(dT) cellulose. The amount of mRNA recovered was quantitated by UV spectrophotometry. The cDNA was synthesized with either 2.0 µg or 5.0 µg of mRNA by random hexamer priming using a 1st strand™ cDNA synthesis kit (CLONTECH). The efficiency of the cDNA synthesis was estimated using glucose 3-phosphate dehydrogenase (G3PDH) amplimers (Clontech, Palo Alto, Calif., USA) as a positive control.

EXAMPLE 3

Quantitative PCR mRNA overexpression of antileukoprotease was determined using a quantitative PCR approach as previously reported (19–21). The ALP target sequences were amplified in parallel with the β-tubulin gene. β-tubulin has previously been established to be a consistently expressed internal control for both normal and tumor tissues (19,21). The following specific oligonucleotide primers were used for antileukoprotease amplification by PCR: Primer set 1—forward 5'-TGCATTGACAACGAGGC-3' (SEQ ID No. 1) and reverse 5'-CTGTCTTGACATTGTTG-3' (SEQ ID No. 2); and, primer set 2—forward 5'-CCTTCAAAGCTGGAGTCTGT-3' (SEQ ID No. 3) and reverse (CCAAAGGAGGATATCAGTGG-3' (SEQ ID No. 4). The primers for the β-tubulin internal control amplification were, forward 5'-CGCATCAACGTGTACTACAA-3'

(SEQ ID No. 5) and reverse 5'-TACGAGCTGGTGGACTGAGA-3' (SEQ ID No. 6). The predicted sizes of the amplified gene were 400 bp for ALP primer set 1, 469 bp for ALP primer set 2 and 454 bp for β-tubulin. The primer sequences used in this study were designed according to the cDNA sequences described for antileukoprotease and by Hall et al. for β-tubulin (22).

The PCR reaction mixture consisted of cDNA derived from 50 ng of mRNA, 5 pmol of sense and antisense primers for both the stratum corneum chymotryptic enzyme gene and the β-tubulin gene, 200 μmol of dNTPs, 5 μCi of [α-$^{32}$P]dCTP and 0.25–0.625 units of Taq DNA polymerase with reaction buffer (Promega) in a final volume of 25 μl. The target sequences were amplified in parallel with the β-tubulin gene. Thirty cycles of PCR were carried out in a Thermal Cycler (Perkin-Elmer Cetus, Foster City, Calif., USA). Each cycle of PCR included 30 seconds of denaturation at 95° C., 30 seconds of primer annealing at 58–60° C. and 30 seconds of extension at 72° C. It was previously established (19,21) and confirmed for the stratum corneum chymotryptic enzyme that co-amplification with β-tubulin under these conditions for 30 cycles remains linear for both products. Tubes containing all ingredients except templates were included in all runs as negative control reactions.

The PCR products were separated on 2% agarose gels and the radioactivity of each PCR product was determined by using a Phospho Imager (Molecular Dynamics). In the present study, the gene expression of the stratum corneum chymotryptic enzyme was calculated as the ratio of ALP to β-tubulin as measured by the phospho imager. The overexpression cut-off value was defined at two standard deviation above the mean expression level for normal ovarian expression. For statistical analysis, the $\chi^2$ test and Fischer's exact probability were used for contingency analysis and the unpaired student's T-test was used for the comparison of the mean values of normal ovary and tumors. Significance was defined as $p<0.05$.

EXAMPLE 4
Northern Blot Analysis

Ten μg of mRNA were loaded onto a 1% formaldehyde-agarose gel, resolved by electrophoresis and blotted on a Hybond-N+ nylon membrane (Amersham, Amersham, UK). $^{32}$P-labeled cDNA probes were made by Prime-a-Gene Labeling System (Promega, Madison, Wis.). The PCR products were amplified using the specific primers described above as probes. The blots were prehybridized for 30 min and hybridized for 60 min at 68° C. with a $^{32}$P-labeled cDNA probe in ExpressHyb Hybridization Solution (CLONTECH, Palo Alto, Calif.). Control hybridization to determine relative gel loading was performed with the β-tubulin probe.

Normal human tissues including spleen, thymus, prostate, testis, ovary, small intestine, colon, peripheral blood leukocyte, heart, brain, placenta, lung, liver, skeletal muscle, kidney, pancreas and normal human fetal tissues; brain, lung, liver and kidney (Human Multiple Tissue Northern Blot; CLONTECH, Palo Alto, Calif.) were all examined using the same hybridization procedure.

EXAMPLE 5
Immunohistochemistry

Polyclonal rabbit antibodies were generated by immunization with a poly-lysine linked multiple antigen peptide (a 12 amino acid sequence near the carboxy terminal end of ALP). Immunohistochemical localization of antileukoprotease antigen was examined using normal ovaries, mucinous LMP tumor and adenocarcinomas (including serous adenocarcinomas, mucinous adenocarcinoma and clear cell carcinomas) in the same series of the samples as were used for mRNA isolation. Formalin fixed and paraffin-embedded sections, 4 μm thick, were cut and mounted o n aminopropyltriethoxysilane treated slides. Slides were routinely deparaffinized with xylene and rehydrated with a series of ethanol washes. Nonenzymatic antigen retrieval was performed by microwave heat treatment seven times for three minutes in a 0.01 M sodium citrate buffer (pH 6.0). Immunohistochemical staining was performed manually using the avidin-biotin peroxidase complex technique (Vectastain Elite ABC kit, Vector Laboratories, Burlingame, Calif., USA).

This indirect immunoperoxidase staining procedure was performed at room temperature. Endogenous peroxidase and nonspecific background staining were blocked by incubating the slides with methanol containing 0.3% $H_2O_2$ for 30 minutes. The slides were washed with phosphate-buffered saline (PBS) for 30 minutes, blocked with normal goat serum for thirty minutes, and incubated with the above rabbit anti-antileukoprotease polyclonal antibody for two hours. After washing with phosphate-buffered saline (PBS) for 30 minutes, sections were incubated with biotinylated anti-rabbit IgG for 30 minutes. After washing with PBS for 30 minutes, slides were incubated with ABC reagent for 30 minutes. The final products were visualized using the 3-amino-9-ethylcarbazole (AEC) substrate system (DAKO Corporation, Carpinteria, Calif.) and were counterstained with Mayer hematoxylin for 20 seconds before mounting. Positive controls and negative controls were used for each section. Normal endocervix was used a s a positive control. Negative controls were prepared by using normal rabbit serum on sections instead of the primary antibody. All experiments were duplicated. The stained slides were examined microscopically by 3 observers. The presence of more than 10% focally distributed positive tumor cells was the criterion for a 1+ positive staining and more than 50% of positive tumor cells was the criterion for a 2+ positive staining. When less than 10% of the cells showed positive nuclear staining, the staining was considered negative EXAMPLE 6
Western Blot Approximately 20 ng of MDA-MBA-435S and HeLa cell lysates were separated on a 15% SDS-PAGE gel and electroblotted to PVDF at 100 V for 40 minutes at 4° C. The proteins were fixed to the membrane by incubation in 50% MeOH for 10 minutes. The membrane was blocked overnight in TBS, pH 7.8 containing 0.2% non-fat milk. Primary antibody was added to the membrane at a dilution of 1:100 in 0.2% milk/TBS and incubated for 2 hours at room temperature. The blot was washed and incubated with a 1:3000 dilution of alkaline-phosphatase conjugated goat anti-rabbit IgG (BioRad) for one hour at room temperature. The blot was washed and incubated with a chemiluminescent substrate before a 10 second exposure to X-ray film for visualization.

Figure 1:
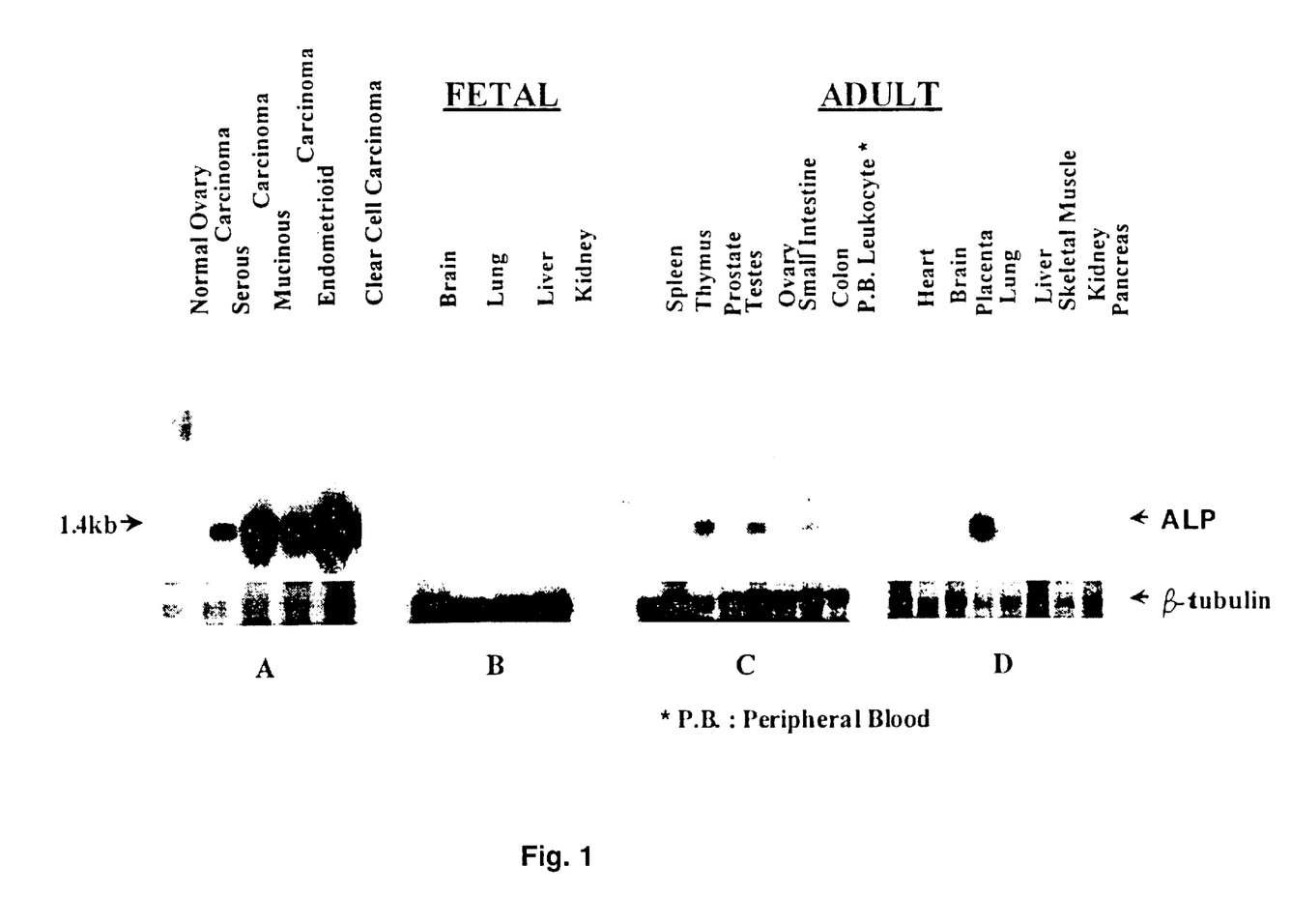
FIGS. 1A–1D show the results of northern blot analysis of antileukoprotease expression in various tissues.

EXAMPLE 7
Northern Blot Analysis of Antileukoprotease Expression in Ovarian Carcinomas To evaluate the mRNA expression of antileukoprotease in ovarian tumors and to examine the size of the mRNA transcript, Northern blot analysis with a $^{32}$P-labeled antileukoprotease probe was performed in representative cases of each type of ovarian carcinoma (FIG. 1A). Northern blot analysis revealed a 1.4 kb transcript in all of the subtypes of ovarian carcinoma including serous, mucinous, endometrioid, and clear cell carcinomas (FIG. 1A, lanes 2–4). No transcript was observed in normal ovarian tissue (FIG. 1A, lane 1). These results demonstrate that an appropriately sized transcript of the antileukoprotease gene is expressed in the ovarian carcinomas.

EXAMPLE 8
Northern Blot Analysis of Antileukoprotease Expression in Normal Tissues Northern blot analysis with a $^{32}$P-labeled antileukoprotease probe was also performed in normal fetal and adult tissue samples. In the fetal tissues, little or no antileukoprotease expression was detected in fetal brain, lung, liver, kidney and pancrease (FIG. 1B). Antileukoprotease transcript was also not detected in many normal adult tissues, including heart, brain, placenta, liver, skeletal muscle, kidney, and pancreas (FIGS. 1C and 1D). Only adult lung showed an abundance of the antileukoprotease transcript (FIG. 1D). Lower levels of expression were observed in adult prostate, ovaries, and the colon (FIG. 1C). Further data supporting tumor expression of antileukoprotease was obtained using polyclonal antibodies developed to multiple antigen peptide (MAP peptide), a 12 amino acid sequence near the carboxyl terminal of antileukoprotease (data not shown).

EXAMPLE 9
Semi-quantitative PCR Analysis of Antileukoprotease (ALP) Overexpression.

Figure 2:
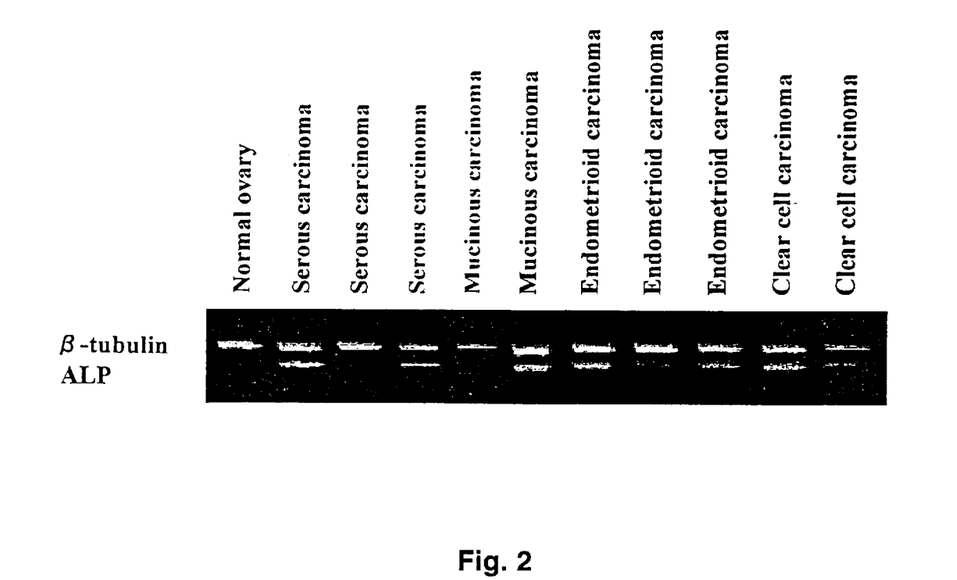
FIG. 2 shows the overexpression of antileukoprotease in ovarian carcinoma specimens as detected by quantitative PCR of antileukoprotease transcript. Expression levels of antileukoprotease relative to β-tubulin are significantly elevated in many cancer samples relative to levels observed in normal ovary.

To confirm the results of the northern blot analysis, semi-quantitative PCR was performed with primers for antileukoprotease and the β-tubulin internal control on 34 ovarian carcinomas and 10 normal ovarian tissue samples. FIG. 2 shows an example of a semi-quantitative PCR evaluation of antileukoprotease expression using oligonucleotides specific for antileukoprotease and the β-tubulin internal control. It was apparent that many ovarian carcinoma samples, when compared to normal ovarian samples, exhibit elevated levels of antileukoprotease transcript relative to the levels of the control β-tubulin transcript, providing additional evidence that antileukoprotease is often overexpressed in ovarian carcinoma specimens.

The relative expression antileukoprotease of ALP and β-tubulin in each sample were measured by phospho imager analysis. The results for each tissue sample are presented in Table 1. It can be noted that many low malignant potential tumors and most carcinomas have a statistically significant overexpression of antileukoprotease. In many cases, this expression exceeds the mean for normal by 4SD. It should also be noted that in at least one ovarian tumor cell line, CAOV3, significant overexpression of antileukoprotease was observed (Table 1).

TABLE 1

A complete analysis of expression comparing normal ovarian tissue to low malignant potential tumors and to overt carcinomas

| Lab No. | Hist. Type | ALP | alp |
|---|---|---|---|
| 456 | normal ovary | 0.0033 | 0 |
| 856 | normal ovary | 0.0228 | 0 |
| 858 | normal ovary | 0.0246 | 0 |
| 1235 | normal ovary | 0.04 | 0 |
| 1338 | normal ovary | 0.0997 | 0 |
| 1339 | normal ovary | 0.1058 | 0 |
| 1343 | normal ovary | 0.0433 | 0 |
| 1344 | normal ovary | 0.1014 | 0 |
| 1345 | normal ovary | 0.069 | 0 |
| 2296 | normal ovary | 0.0146 | 0 |
| 481 | s adenoma (LMP) | 0.3214 | 4+ |
| 1448 | s adenoma (LMP) | 0.0251 | 0 |
| 1452 | s adenoma (LMP) | 0.2815 | 4+ |
| 1444 | s adenoma (LMP) | 0.5005 | 4+ |
| 1447 | s adenoma (LMP) | 0.3741 | 4+ |
| 1450 | s adenoma (LMP) | 0.2195 | 4+ |
| 1036 | m adenoma (LMP) | 0.0775 | 0 |
| 1451 | m adenoma (LMP) | 0.0515 | 0 |
| 1456 | m adenoma (LMP) | 0.2771 | 4+ |
| 1242 | s carcinoma | 0.1502 | 2+ |
| 515 | s carcinoma | 1.5101 | 4+ |
| 1032 | s carcinoma | 0.28 | 4+ |
| 1240 | s carcinoma | 1.2282 | 4+ |
| 1245 | s carcinoma | 0.9342 | 4+ |
| 465 | s carcinoma | 0.8166 | 4+ |
| 1026 | s carcinoma | 0.4244 | 4+ |
| 464 | s carcinoma | 0.0827 | 0 |
| 468 | s carcinoma | 0.5117 | 4+ |
| 1033 | s carcinoma | 0.036 | 0 |
| 1039 | s carcinoma | 0.1749 | 2+ |
| 960 | s carcinoma | 0.3775 | 4+ |
| 962 | s carcinoma | 0.446 | 4+ |
| 1819 | s carcinoma | 0.5974 | 4+ |
| 1443 | m carcinoma | 0.1122 | 0 |
| 1219 | m carcinoma | 0.8489 | 4+ |
| 1990 | m carcinoma | 1.3723 | 4+ |
| 484 | m carcinoma | 0.0007 | 0 |
| 1244 | m carcinoma | 0.0376 | 0 |
| 1816 | m carcinoma | 0.4697 | 4+ |
| 2295 | e carcinoma | 0.2437 | 4+ |
| 2299 | e carcinoma | 0.4789 | 4+ |
| 2300 | e carcinoma | 0.4094 | 4+ |
| 947 | c carcinoma | 0.5468 | 4+ |
| 948 | c carcinoma | 0.5086 | 4+ |
| sw626 | ovarian cancer cell line | 0.0633 | 0 |
| caov3 | ovarian cancer cell line | 0.1862 | 2+ |

| | |
|---|---|
| Mean | 0.05245 |
| Confidence level (95.0%) | 0.02769603 |
| Standard Error | 0.01224319 |
| Median | 0.04165 |
| Mode | #Num! |
| Standard Deviation | 0.03871635 |
| Mean+2SD | 0.12989 = 2+ |
| Mean+4SD | 0.20733 = 4+ |
| Sample Variance | 0.00149896 |
| Kurtosis | −1.60048588 |
| Skewness | 0.37295213 |
| Range | 0.1025 |
| Minimum | 0.0033 |
| Maximum | 0.1058 |
| Sum | 0.5245 |
| Count | 10 |

EXAMPLE 10
Statistical Analysis Semi-quantitative PCR Results

Figure 3:
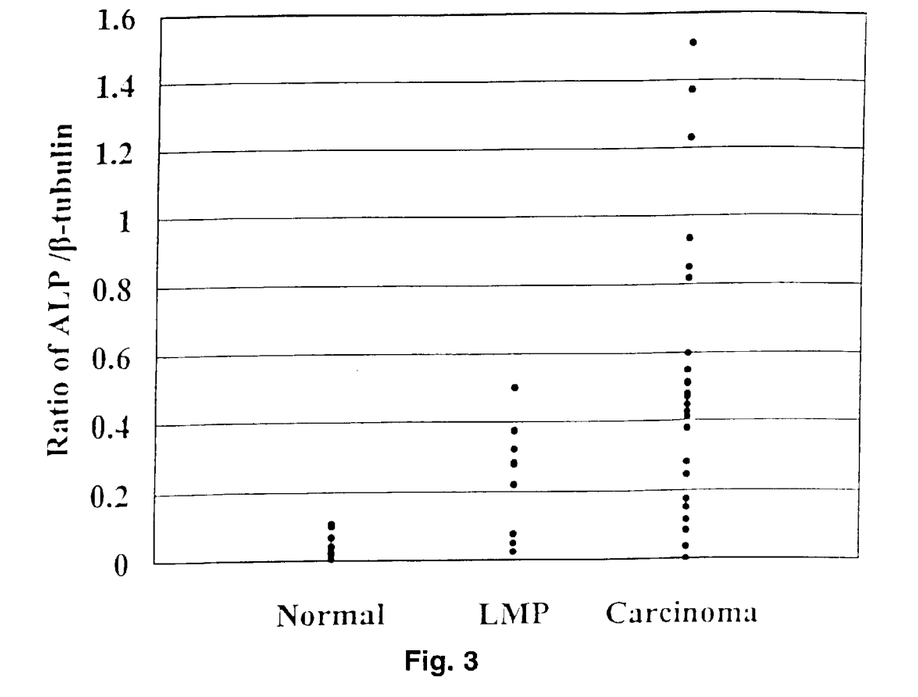
FIG. 3 shows a graphical representation of antileukoprotease/β-tubulin ratios in normal ovaries, LMP tumors, and carcinomas. ALP mRNA expression levels were significantly elevated in IMP tumors and carcinomas as compared with levels in normal ovaries.

FIG. 3 summarizes the relative expression ratios of antileukoprotease to β-tubulin in normal ovaries, LMP tumors, and ovarian carcinomas. The exact ratios (mean±SD) are listed in Table 2 for normal ovary (0.05±0.04), LMP tumor (0.24±0.16) and carcinoma (0.50±0.41). In many carcinoma cases as well as LMP tumors, antileukoprotease mRNA expression was significantly elevated compared to that in normal ovary (LMP tumor, p<0.01; carcinoma, p<0.01; unpaired T-test). There was no statistical difference between the antileukoprotease expression levels and the clinical stage, histological grade or histological type. It should be noted that in one ovarian cancer cell line, CaOv3, significant overexpression of antileukoprotease was observed (ratio= 0.19), while another cell line, SW626, showed, a relatively low level of antileukoprotease expression (ratio=0.06) (Table 1).

TABLE 2

Relative Expression Levels of ALP and ALP Overexpression Rates in Ovarian Tumors

| Tissue Type | N | Ratio ALP/β-tubulin Mean | SD | ALP overexpression rates[a] |
|---|---|---|---|---|
| Normal Ovary | 10 | 0.05 | 0.04 | 0/10 (0%) |
| LMP Tumor | 9 | 0.24[b] | 0.16 | 6/9 (67%) |
| Serous | 6 | 0.29 | 0.16 | 5/6 (83%)[d] |
| Mucinous | 3 | 0.14 | 0.12 | 1/3 (33%) |
| Ovarian Cancer | 25 | 0.50[c] | 0.41 | 20/25 (80%) |
| Clinical Stage | | | | |
| Stage 1/2 | 7 | 0.54 | 0.45 | 6/7 (86%) |
| Stage 3 | 18 | 0.49 | 0.41 | 14/18 (78%) |
| Histological Grade | | | | |
| Grade 1/2 | 13 | 0.62 | 0.52 | 10/13 (77%) |
| Grade 3 | 12 | 0.38 | 0.22 | 10/12 (83%) |
| Histological Type | | | | |
| Serous | 14 | 0.54 | 0.44 | 12/14 (86%) |
| Mucinous | 6 | 0.47 | 0.55 | 3/6 (50%) |
| Endometrioid | 3 | 0.38 | 0.12 | 3/3 (100%) |
| Clear Cell | 2 | 0.53 | 0.03 | 2/2 (100%) |

[a]Overexpression was defined as ≧2 SD over the mean normal value
[b]Significant, LMP tumor vs. normal ovary; p<0.01, unpaired T test
[c]Significant, cancer vs. normal ovary; p<0.01, unpaired T test
[d]Significant, serous tumors (17/20) vs. mucinous tumors (4/9), p<0.05, $\chi^2$ test Table 2 also summarizes the mean antileukoprotease overexpression rates by tissue subtypes in ovarian tumors. Overall, antileukoprotease mRNA overexpression was found in 6 of 9 LMP tumors (67%) and in 20 of 25 carcinoma cases (80%). All 10 normal ovaries showed relatively low levels of antileukoprotease mRNA expression. With regard to histological type, increased expression of antileukoprotease was found in 5 of 6 LMP serous tumors (83%) and in 12 of 14 serous carcinomas, whereas only 1 of 2 LMP mucinous tumors (33%) and 3 of 6 mucinous carcinomas (50%) showed overexpression of antileukoprotease. Thus, there was a statistical difference of the antileukoprotease overexpression rates between serous tumors (17/20) and mucinous tumors (4/9) including LMP tumors and carcinomas (p<0.05, $\chi^2$ test). The antileukoprotease overexpression rates determined for clinical stage and histological grad did not show any significant difference.

Table 3 indicates the relationship between antileukoprotease and SCCE overexpression status in ovarian tumor cases including LMP tumors and carcinomas. SCCE overexpression status was analyzed in the same series of the samples. Out of twenty-six antileukoprotease overexpression cases, 23 cases showed SCCE overexpression, whereas only two out of eight cases showed SCCE overexpression with normal expression of antileukoprotease. Thus, there was a significant positive correlation between antileukoprotease and SCCE overexpression status in ovarian tumor cases (p<0.01, $\chi^2$ test).

TABLE 3

ALP and SCCE Overexpression Status in Ovarian Tumors Including LMP Tumors and Carcinomas

| | SCCE mRNA Expression | |
|---|---|---|
| ALP mRNA Expression | SCCE Overexpression[a] Cases | SCCE Normal Range[b] Cases |
| ALP Overexpression[a] Cases | 23 | 3 |
| ALP Normal Range[b] Cases | 3 | 6 |

(p<0.01, $\chi^2$ Test)
[a]Overexpression was defined as >2 SD over the mean normal value
[b]Normal range = mean ± 2SD for normal ovary value

EXAMPLE 11

Immunohistochemical Analysis

Figure 4A:
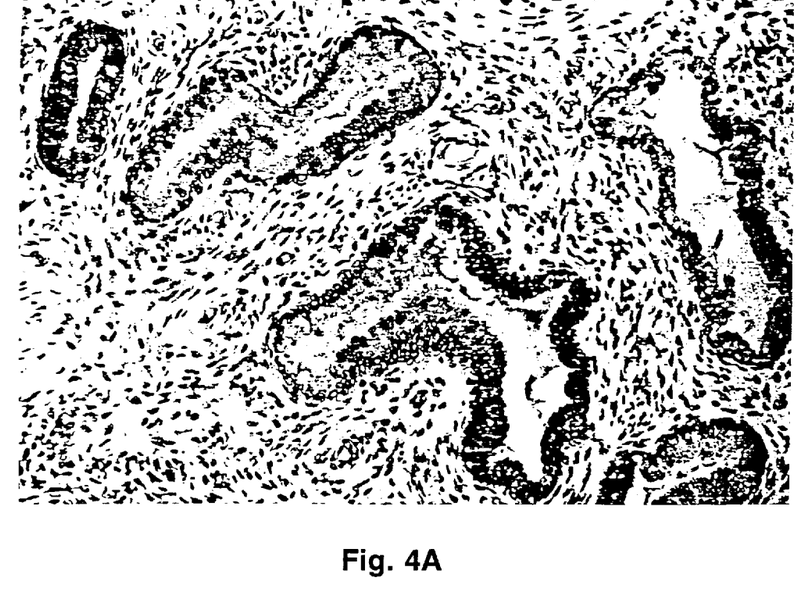
FIGS. 4A–4E show immunohistochemical staining results for antileukoprotease in various ovarian tumors.
Figure 4B:
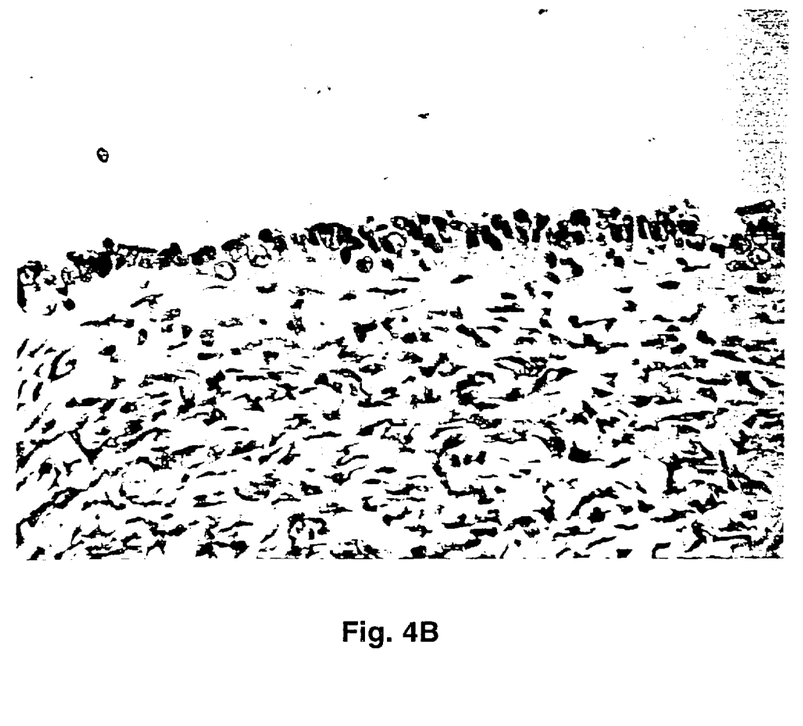

To further confirm the presence of the antileukoprotease protein in ovarian tumor cells. Antileukoprotease expression in both normal ovarian epithelia and ovarian tumor tissues was analyzed by immunohistochemical staining with the polyclonal serum describe supra. A comparison of immunohistochemical staining of normal ovary and various subtypes of ovarian carcinoma is shown in FIGS. 4A–4G. Different patterns of staining were noted in tumor cell cytoplasm, vesicles and membranes. In a normal endocervical specimen, which was used as a positive control, antileukoprotease protein was detected in endocervical glandular cells as well as on the mucin in the gland (FIG. 4A). Little or no staining was observed with normal ovarian surface epithelium (FIG. 4B). However, positive staining was observed both in the cytoplasm and on the cell membrane of ovarian cancer cells (FIG. 4C; (endometrioid adenocarcinoma).

Figure 4C:
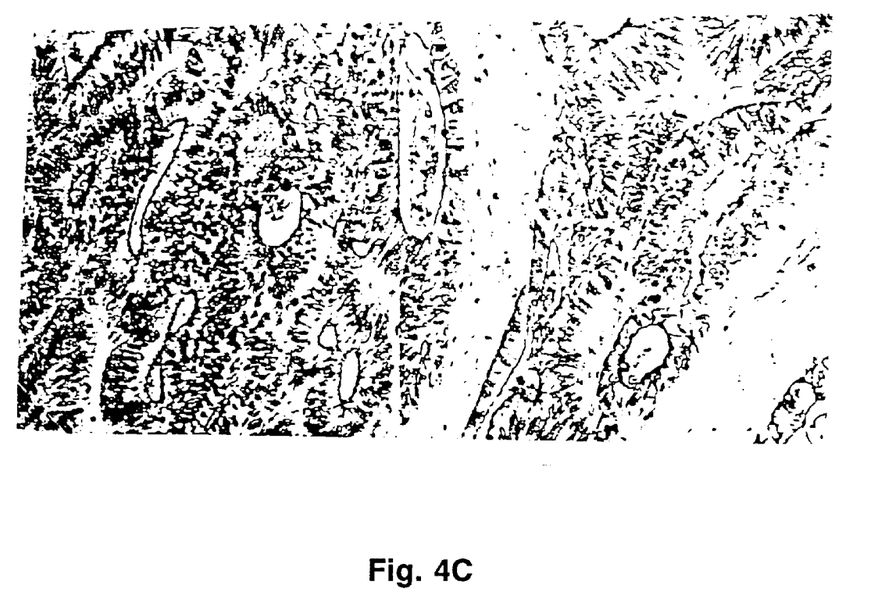
Figure 4D:
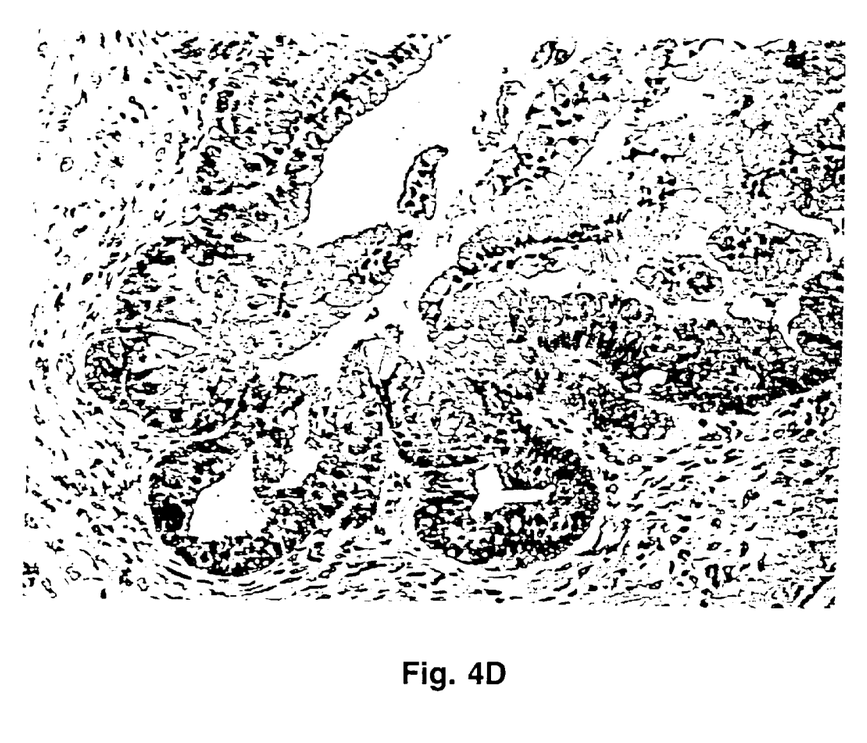
Figure 4E:
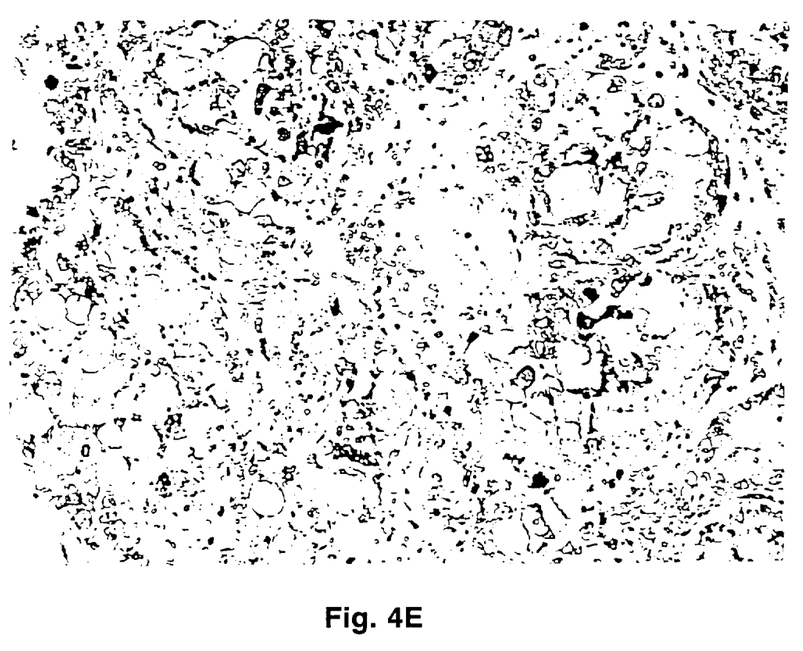
Figure 4F:
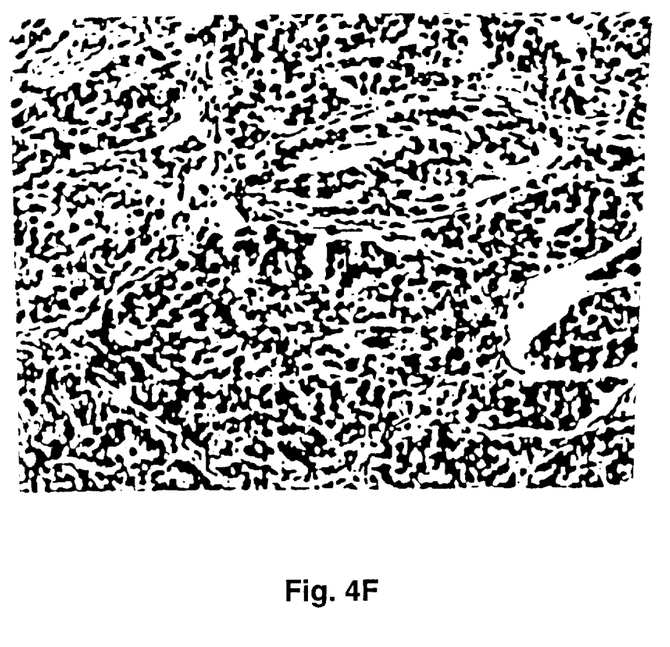
Figure 4G:
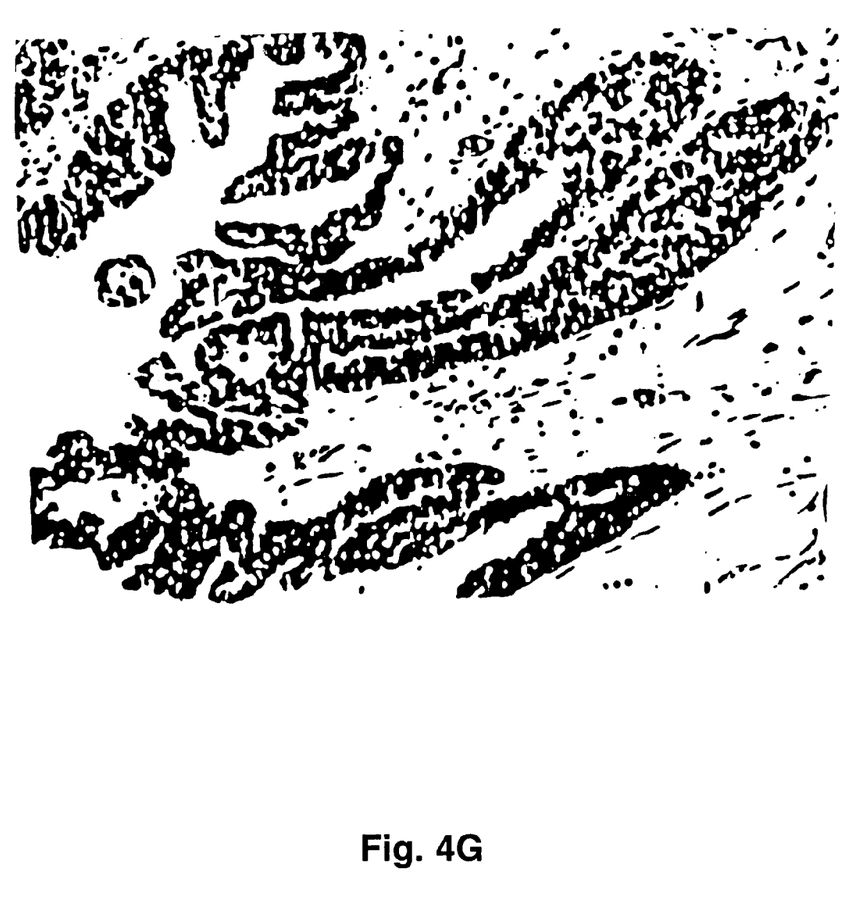

Positive antileukoprotease staining was observed on the mucin as well as in the tumor glands of mucinous carcinoma (FIG. 4D). The secretion of clear cell carcinomas also stained positive for antileukoprotease (FIG. 4E). The extracellular location of antileukoprotease was especially detectable in endometrioid and clear cell tumors (FIGS. 4C and 4E respectively). Serous carcinomas were also positive for ALP immunohistochemical staining (FIGS. 4F and 4G). More than 10% positive tumor cell staining of ALP was detected in one of two (50%) benign adenomas, two (100%) of two LMP tumors, and 17 of 25 (68%) adenocarcinomas while little or no staining was observed in all three normal ovary specimens. A more complete analysis of the immunohistochemical findings is presented in Table 4.9 out of 12 borderline and low malignant potential tumors stained positively for antileukoprotease while 12 out of 19 carcinomas showed positive staining.

TABLE 4

A complete analysis of ALP immunohistochemical findings

| Case | Stage | Histology | Grade | ALP | Prognosis |
|---|---|---|---|---|---|
| 1 | | normal ovary | | 0– | |
| 2 | | normal ovary | | 0– | |
| 3 | | normal ovary | | 0– | |
| 4 | | mucinous B | | 0– | Alive |
| 5 | | mucinous B | | 2+ | Alive |
| 6 | 1a | serous LMP | G1 | 1+ | Alive |
| 7 | 1a | mucinous LMP | G1 | 1+ | Alive |
| 8 | 1a | mucinous ca | G1 | 1+ weak | Alive |
| 9 | 1a | mucinous ca | G2 | 0– | Alive |

TABLE 4-continued

A complete analysis of ALP immunohistochemical findings

| Case | Stage | Histology | Grade | ALP | Prognosis |
|---|---|---|---|---|---|
| 10 | 1a | endometrioid ca | G1 | 2+ | Alive |
| 11 | 1c | serous ca | G1 | 1+ | Alive |
| 12 | 1c | mucinous ca | G1 | 2+ | Alive |
| 13 | 1c | mucinous ca | G1 | 2+ | Alive |
| 14 | 1c | clear cell ca | G2 | 1+ | Alive |
| 15 | 1c | clear cell ca | G2 | 0− | Alive |
| 16 | 2c | serous ca | G3 | 1+ | Alive |
| 17 | 3a | mucinous ca | G2 | 2+ | Alive |
| 18 | 3b | serous ca | G1 | 2+ | Alive |
| 19 | 3c | serous ca | G1 | 0− | Dead |
| 20 | 3c | serous ca | G3 | 0− | Alive |
| 21 | 3c | serous ca | G2 | 2+ | Alive |
| 22 | 3c | serous ca | G1 | 2+ | unknown |
| 23 | 3c | serous ca | G3 | 0− | Alive |
| 24 | 3c | serous ca | G2 | 0− | Dead |
| 25 | 3c | mucinous ca | G1 | 2+ | Dead |
| 26 | 3c | mucinous ca | G2 | 2+ | unknown |
| 27 | 3c | endometrioid ca | G2 | 1+ | Alive |
| 28 | 3c | endometrioid ca | G1 | 0− | Dead |
| 29 | 3c | endometrioid ca | G2 | 0− | Alive |
| 30 | 3c | endometrioid ca | G2 | 1+ | Dead |
| 31 | 3c | endometrioid ca | G3 | 2+ | Alive |
| 32 | 3c | clear cell ca | G3 | 2+ | Dead |

B Borderline
ca carcinoma
LMP Low malignant potential

EXAMPLE 12

Analysis and Implications of ALP Expression in Ovarian Tumors

In recent years, aberrant expression of serine proteases such as plasminogen activator has been shown to correlate positively with the invasiveness and metastatic potential of tumor cells (9). More significantly, the serine protease known as prostate-specific antigen (PSA) has been used successfully as a tumor marker for the early diagnosis of prostate cancer (23). Serine proteases play important roles in the cascade of events involved in the malignant processes, and at least for prostate cancer, provide sufficient signal to allow detection of early disease.

Specific inhibitors for most of the proteolytic enzymes have been identified and it has been contemplated that these inhibitors inhibit extracellular degradation, which in turn prevents tumor cell invasion. For example, plasminogen-activator-inhibitor 1 is suggested to protect the tumor stroma from ongoing urokinase-plasminogen-activator mediated proteolysis in many human tumors (24). The proteolytic activity associated with tumors is probably a highly regulated cascade and the interplay between proteases and their inhibitors may play a specific role in tumor development and progression.

In the process of studying protease enzymes in ovarian tumors, several candidate genes have been identified to be overexpressed. In an effort to identify other genes which are overexpressed early in the carcinogenic progression of ovarian cancer, a screening strategy was developed using redundant primers to evolutionary conserved domains of extracellular proteases such as the conserved catalytic triad domain of the serine protease family (viz. His—Asp—Ser). In the present study, antileukoprotease, a specific inhibitor of SCCE, was found in be expressed in abundance in carcinoma tissues, with little or no expression in normal ovary.

Antileukoprotease (ALP) is a mucosal secretory protein that has been identified as a potent protease inhibitor of leukocyte serine proteases (18). Antileukoprotease is a secreted protein with a distribution of cysteines known to provide extraordinary stability to inhibitors. Immunocytochemical localization studies have revealed its presence in respiratory tissues, salivary gland, cervical gland, and lacrimal gland (25). Moreover, antileukoprotease can be extracted from the human stratum corneum and is constitutively produced and released from human keratinocyte cell cultures (26). Therefore, Wiedow et al. (27) have suggested that antileukoprotease might not only regulate serine protease activities in mucus secretions but in skin as well.

Recently, Franzke et al. (17) reported that antileukoprotease is the major inhibitor of SCCE in the epidermis and that it seems to be involved in the regulation of desquamation under physiological and pathological conditions. In vivo, SCCE mRNA is expressed in the upper spinous and granular layers of the epidermis (15, 16), and active SCCE can be isolated from human horny layers (13). The fact that inhibition of SCCE causes the concomitant complete inhibition of cell shedding from plantar stratum corneum (desquamation) in vitro (28) led to the hypothesis that SCCE may be involved in the process of physiological desquamation (13–16,28). The fact that SCCE is overexpressed in ovarian tumors supports the potential of SCCE as a target for inhibition of down regulation in therapeutic interventions aimed at preventing the spread or metastasis of ovarian cancer.

Herein, Northern blot hybridization has shown that the antileukoprotease transcript is abundant in ovarian carcinomas but is not detected in normal ovaries. Semi-quantitative PCR analysis supports the observation that antileukoprotease mRNA levels are significantly higher in ovarian tumors as compared to normal ovaries. These results were confirmed by immunohistochemistry experiments which confirmed that antileukoprotease is present in ovarian tumor cells and the mucin secreted therefrom, whereas little or no staining is observed in normal ovarian surface epithelium.

Positive correlation has been demonstrated between SCCE and antileukoprotease mRNA overexpression in ovarian tumor samples including LMP tumors and carcinomas. This observation is, in one sense, paradoxical, since antileukoprotease levels would be expected to be low if SCCE plays an important role during ovarian cancer development and progression. However, the present results demonstrate that co-transcriptional activation SCCE and antileukoprotease seems to occur during transformation and initial tumor growth of ovarian cancer. These data are entirely consistent with similar data observed for SCCE/ALP expression in differentiated keratinocytes. In light of the fact that desquamation of skin cells is SCCE dependent and can be inhibited by ALP, it is suggested that some dis-synchrony in time or space allows SCCE activation in the presence of ALP.

The present findings show that the presence of SCCE and antileukoprotease together in tumor cells may similarly allow the shedding or desquamation of malignant cells through a similar dis-synchrony. The fact that inhibition of SCCE activity prevents normal desquamation of skin cells points to the potential of SCCE as a target for inhibition or down regulation of the spread or metastasis of ovarian carcinoma. Because antileukoprotease is a specific inhibitor of SCCE, it may also be useful in the abatement of tumor growth and progression in low-antileukoprotease-expressing ovarian cancers, although there is already high-level-ALP expression observed in many ovarian cancers.

It has been demonstrated herein that the overexpression of antileukoprotease is a common event in ovarian tumors. Because antileukoprotease is a secreted protein and antileukoprotease appears in abundance only in tumor tissues as demonstrated by Northern blot analysis and semi-quantitative analyses, it has a potential for being present in the circulation of tumor-bearing patients. The overexpression of antileukoprotease in LMP tumors and stage I carcinomas is of particular note as the antileukoprotease is produced directly by tumor cells instead of underlying stromal tissues. As a result of this, assays may be developed for the early detection of ovarian cancer based on the detection the antileukoprotease protein. This molecule fulfills many criteria necessary for a valuable marker of tumor growth and progression. It is overexpressed in tumor cells secreted to the extracellular space and is a relatively small protein (approximately 100 amino acids) providing good opportunity for uptake into the circulation. Moreover, antileukoprotease is a very stable protein providing potential for a relatively long half life in the circulation. In addition, even though antileukoprotease has been shown to directly inhibit SCCE activity, it co-existence with SCCE during desquamation of keratinocytes suggests that a similar mechanism of antileukoprotease sequestration of lack of ability to inhibit SCCE may allow the desquamation or shedding of ovarian tumor cells.

The following references were cited herein.
1. Neurath, H. The diversity of proteolytic enzymes. In: Beynon et al., (eds.), Proteolytic enzymes, Oxford, IRL Press 1989:1–13.
2. Liotta, et al., *Cell* 1991; 64:327–336.
3. Duffy, M. J. *Clin Exp Metastasis* 1992; 10:145–155.
4. Tryggvason, et al., *Biochem Biophys Acta* 1987; 907:191–217.
5. Powell, W. C. et al., *Cancer Res* 1993, 53:417–422.
6. MacDougall, J. R. et al., *Cancer and Metastasis Reviews* 1995; 14:351–362.
7. Rempel, S. A. et al., *Cancer Res* 1994; 54:6027–6031.
8. Nazeer, T. et al., *Am J Clin Pathol* 1992; 97:764–769.
9. Duffy, M. J. et al., *Cancer* (Phila) 1988; 62:531–533.
10. Liotta, L. A. et al., *Cell* 1991; 64:327–336.
11. Wang, M. et al., *Cancer Res* 1988; 48:6262–6271.
12. Reich, R. et al., *Cancer Res* 1988; 48:3307–3312.
13. Egelrud, T. *J Invest Dermatol* 1993; 101:200–204.
14. Hansson, et al., *J Biol Chem* 1994;269:19420–19426.
15. Sondell, et al., *J Histochem Cytochem* 1994;42:459–465.
16. Sondell, et al., *J Invest Dermatol* 1995; 104:819–823.
17. Franzke, et al., *J Biol Chem* 1996;271:21886–21890.
18. Thompson, R. C., et al., *Proc Natl Acad Sci USA* 1986; 83:6692–6696, 1986.
19. Shigemasa, et al., *J Soc Gynecol Invest* 1997;4:95–102.
20. Tanimoto, et al., *Gynecol Oncol* 1997;66:308–312.
21. Shigemasa, K. et al., *Int J. Gynecol Cancer* 1997, 7(4):296–303.
22. Hall, et al., *Mol Cell Biol* 1983; 3:854–862.
23. McCormack, R. T. et al., *Urology* 1995; 45:729–744.
24. Pappot et al., *Biol Chem Hoppe Seyler* 1995; 376(5):259–267
25. Franken C. et al., *J Histochem Cytochem* 1989; 37:493–498.
26. Wiedow, O. (1995) *Isolierung und Charakterisierung von Serinprotease Inhibitoren der menschlichen Epidermis*, Köster, Berlin
27. Wiedow, O. et al., *J Invest Dermatol* 1993; 101:305–309.
28. Lundstrom, A. et al., *J Invest Dermatol* 1988; 91:340–343.
29. Garver, R. I. et al., *Gene Ther* 1994; 1:46–50.
30. Lunderström et al.,. (1988) *J. Invest. Dermatol.* 101, 200–204.

Any patents or publications mentioned in this specification are indicative of the levels of those skilled in the art to which the invention pertains. These patents and publications are herein incorporated by reference to the same extent as if each individual publication was specifically incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of detecting an ovarian tumor in an individual, comprising the step of:

measuring a level of antileukoprotease in a sample from said individual, wherein if said level of antileukoprotease exceeds a mean basal level of antileukoprotease in nondiseased individuals by 2 standard deviations or greater, said individual has said ovarian tumor.

2. The method of claim 1, wherein said tumor is selected from the group consisting of a low malignant potential tumor and an ovarian carcinoma.

3. The method of claim 2, wherein said ovarian carcinoma is selected from the group consisting of a serous carcinoma, a mucinous carcinoma, an endometrioid carcinoma and a clear cell carcinoma.

4. The method of claim 1, wherein said antileukoprotease is detected in a sample selected from the group consisting of an ovarian secretion, an ovarian biopsy, a metastatic tumor biopsy and blood.

5. The method of claim 1, wherein said antileukoprotease is detected by a method selected from the group consisting of western blot analysis, immunohistochemical staining, and immunochemical methods.

* * * * *